(12) United States Patent
Tazawa et al.

(10) Patent No.: US 11,084,029 B2
(45) Date of Patent: Aug. 10, 2021

(54) CATALYST, ACRYLIC ACID PRODUCTION METHOD, AND CATALYST PRODUCTION METHOD

(71) Applicant: Mitsubishi Chemical Corporation, Chiyoda-ku (JP)

(72) Inventors: Kazuharu Tazawa, Tokyo (JP); Yoshimune Abe, Tokyo (JP); Mitsunobu Ito, Tokyo (JP)

(73) Assignee: Mitsubishi Chemical Corporation, Chiyoda-ku (JP)

(*) Notice: Subject to any disclaimer, the term of this patent is extended or adjusted under 35 U.S.C. 154(b) by 0 days.

(21) Appl. No.: 16/256,323

(22) Filed: Jan. 24, 2019

(65) Prior Publication Data
US 2019/0151835 A1 May 23, 2019

Related U.S. Application Data

(63) Continuation of application No. PCT/JP2017/026694, filed on Jul. 24, 2017.

(30) Foreign Application Priority Data

Jul. 25, 2016 (JP) .............................. JP2016-145419
Apr. 27, 2017 (JP) .............................. JP2017-088647
(Continued)

(51) Int. Cl.
*C07C 51/25* (2006.01)
*B01J 35/02* (2006.01)
(Continued)

(52) U.S. Cl.
CPC ........... *B01J 35/026* (2013.01); *B01J 23/002* (2013.01); *B01J 23/8435* (2013.01);
(Continued)

(58) Field of Classification Search
CPC .............. B01J 2523/00; B01J 2523/41; B01J 2523/53; B01J 2523/847; B01J 23/002;
(Continued)

(56) References Cited

U.S. PATENT DOCUMENTS 3,939,096 A * 2/1976 Richardson .............. B01J 23/34
502/241
4,282,116 A * 8/1981 Reuter .................... B01J 35/026
502/350
(Continued)

FOREIGN PATENT DOCUMENTS

CN 1317369 10/2001
CN 1366579 12/2002
(Continued)

OTHER PUBLICATIONS

JP2010516441 translated (Year: 2010).*
(Continued)

*Primary Examiner* — Yevgeny Valenrod
*Assistant Examiner* — Blaine G Doletski
(74) *Attorney, Agent, or Firm* — Oblon, McClelland, Maier & Neustadt, L.L.P.

(57) ABSTRACT

An object of the present invention is to provide a catalyst ensuring that in the case of causing gas-phase catalytic oxidation of an unsaturated aldehyde and an oxygen-containing gas with use of the catalyst to produce a corresponding unsaturated carboxylic acid, the pressure loss can be kept low and an unsaturated carboxylic acid can be produced with high selectivity. The present invention relates to a ring-shaped or columnar catalyst, which is used at the time of producing a corresponding unsaturated carboxylic acid by causing gas-phase catalytic oxidation of an unsaturated aldehyde and an oxygen-containing gas, wherein the outer peripheral edge part is inclined relative to the center line.

5 Claims, 3 Drawing Sheets

(30) Foreign Application Priority Data

May 17, 2017 (JP) .............................. JP2017-098451
May 17, 2017 (JP) .............................. JP2017-098452

(51) Int. Cl.
| | | |
|---|---|---|
| *B01J 23/843* | (2006.01) | |
| *B01J 37/00* | (2006.01) | |
| *B01J 23/00* | (2006.01) | |
| *C07C 57/04* | (2006.01) | |

(52) U.S. Cl.
CPC ....... *B01J 37/0009* (2013.01); *B01J 37/0045* (2013.01); *C07C 51/252* (2013.01); *B01J 35/02* (2013.01); *B01J 2523/00* (2013.01); *B01J 2523/41* (2013.01); *B01J 2523/53* (2013.01); *B01J 2523/847* (2013.01); *C07C 57/04* (2013.01)

(58) Field of Classification Search
CPC ...... B01J 23/8435; B01J 35/02; B01J 35/026; B01J 37/0009; B01J 37/0045; C07C 51/252; C07C 57/04
See application file for complete search history.

(56) References Cited

U.S. PATENT DOCUMENTS

| | | | |
|---|---|---|---|
| 4,656,157 A * | 4/1987 | Hofmann | B01J 19/30 |
| | | | 502/439 |
| 6,784,134 B2 | 8/2004 | Kasuga et al. | |
| 6,878,847 B2 | 4/2005 | Kasuga et al. | |
| 7,161,044 B2 | 1/2007 | Nakamura et al. | |
| 2001/0029235 A1 | 10/2001 | Walsdorff et al. | |
| 2002/0198103 A1 | 12/2002 | Kasuga et al. | |
| 2003/0181762 A1 | 9/2003 | MacHhammer et al. | |
| 2003/0187298 A1 | 10/2003 | Borgmeier et al. | |
| 2003/0187299 A1 | 10/2003 | MacHhammer et al. | |
| 2004/0082810 A1 | 4/2004 | Borgmeier et al. | |
| 2004/0102648 A1 | 5/2004 | Borgmeier et al. | |
| 2004/0138500 A1 | 7/2004 | Borgmeier | |
| 2004/0199008 A1 | 10/2004 | Kasuga et al. | |
| 2005/0090695 A1 | 4/2005 | Nakamura et al. | |
| 2005/0261520 A1 | 11/2005 | Teshigahara et al. | |
| 2006/0074258 A1 | 4/2006 | Borgmeier et al. | |
| 2010/0016640 A1 * | 1/2010 | Guckel | B01J 19/30 |
| | | | 568/487 |
| 2011/0137078 A1 | 6/2011 | Nakahara et al. | |
| 2016/0244393 A1 | 8/2016 | Kurakami et al. | |

FOREIGN PATENT DOCUMENTS

| | | | |
|---|---|---|---|
| CN | 1697693 | | 11/2005 |
| CN | 1636953 | | 12/2005 |
| CN | 101340975 | | 1/2009 |
| CN | 102046289 | | 5/2011 |
| EP | 0 017 865 A1 | | 10/1980 |
| EP | 0 184 790 A2 | | 6/1986 |
| JP | 55-139834 | | 11/1980 |
| JP | 61-141933 | | 6/1986 |
| JP | 2001-293376 | | 10/2001 |
| JP | 2013202564 | * | 10/2003 |
| JP | 2010516441 | * | 5/2010 |
| JP | 2017-80731 | | 5/2017 |
| RU | 2 285 690 C2 | | 10/2006 |
| RU | 2 312 851 C2 | | 12/2007 |
| TW | 201522301 A | | 6/2015 |
| WO | WO 2007/059974 A1 | | 5/2007 |
| WO | WO 2009/147965 A1 | | 12/2009 |

OTHER PUBLICATIONS

JP2013202564 translated (Year: 2003).*
Extended European Search Report dated Jul. 4, 2019 in European Patent Application No. 17834247.3, 6 pages.
Combined Russian Office Action and Search Report dated Sep. 12, 2019 in Patent Application No. 2019101911 (with English translation ), 18 pages.
International Search Report dated Oct. 3, 2017 in PCT/JP2017/026694, filed on Jul. 24, 2017 (with English Translation).
Written Opinion dated Oct. 3, 2017 in PCT/JP2017/026694, filed on Jul. 24, 2017.
Office Action dated May 18, 2018 in Taiwanese Application 106124899 (with English Translation).
Office Action as received in the corresponding Indian patent application No. 201917002970 dated Feb. 25, 2020 w/English translation, 6 pages.
Office Action as received in the corresponding Japanese patent application No. 2016-150611 dated Sep. 10, 2019 w/Computer generated English translation, 6 pages.
Office Action as received in the corresponding JP Patent Application No. 2017-142765 dated Feb. 16, 2021 w/English Translation, 6 pages.

* cited by examiner

CATALYST, ACRYLIC ACID PRODUCTION METHOD, AND CATALYST PRODUCTION METHOD

TECHNICAL FIELD

The present invention relates to a catalyst. More specifically, the present invention relates to a catalyst which is used at the time of producing a corresponding unsaturated carboxylic acid by causing gas-phase catalytic oxidation of an unsaturated aldehyde and an oxygen-containing gas.

BACKGROUND ART

Conventionally, as to the shape of the catalyst used for producing a corresponding unsaturated carboxylic acid by causing gas-phase catalytic oxidation of an unsaturated aldehyde such as acrolein and an oxygen-containing gas, various shapes have been proposed.

For example, as a catalyst used for selective oxidation from (meth)acrolein to (meth)acrylic acid, Patent Document 1 describes a molded catalyst for a heterogeneous catalyst reaction, which is molded in a hollow cylindrical shape and in which the end face of the hollow cylindrical shape is curved.

Patent Document 2 describes a supported catalyst including an inert support coated with a catalyst powder, characterized in that the inert support has a ring shape with the outer peripheral edge part being curved in the lengthwise direction of the support, which is a catalyst for causing gas-phase catalytic oxidation of propylene, isobutylene, tertiary butyl alcohol or methyl tertiary butyl ether and thereby producing a corresponding unsaturated aldehyde or unsaturated carboxylic acid.

Patent Document 3 describes a supported catalyst for producing a phthalic anhydride containing vanadium and titanium and/or zircon, in which both front faces of an annular support are chamfered obliquely from inside to outside and the length of a cylinder outer wall is shorter at least by 20% than the length of a cylinder inner wall.

Furthermore, Patent Document 4 describes a coated catalyst for oxidation of methanol to formaldehyde, including a nonporous support which is a hollow cylinder with the outer peripheral edge part being inclined at about 60° relative to the center line.

RELATED ART

Patent Document

Patent Document 1: JP-A-S61-141933
Patent Document 2: International Publication: WO2009/147965
Patent Document 3: JP-A-S55-139834
Patent Document 4: US-A-2010-0016640

SUMMARY OF THE INVENTION

Problems That the Invention is to Solve

However, the catalysts described in Patent Documents 1 and 2 had a problem that in the case of producing a corresponding unsaturated carboxylic acid by causing gas-phase catalytic oxidation of an unsaturated aldehyde such as acrolein and an oxygen-containing gas in a reactor filled with the catalyst, the pressure loss is high, the conversion rate of unsaturated aldehyde is low; the selectivity of the corresponding unsaturated carboxylic acid is also low; and in turn, the yield is reduced.

For example, a ring-shaped catalyst may not be uniformly loaded in a reactor, leading to a non-uniform reaction field within the reactor, and a reduction in the conversion rate and selectivity may occur. In the case of a catalyst having a hollow cylindrical shape with the end face being curved, since the catalyst surface area is small for the catalyst volume and the number of reaction active sites is small, the reaction efficiency is low, and the conversion rate or selectivity may be reduced.

Furthermore, in the production of an acrylic acid that is an unsaturated carboxylic acid, a carbide adheres to the catalyst surface. Adhesion of the carbide to the catalyst surface (coking) is likely to occur due to a decrease in the gas amount in a reaction tube suffering from a high pressure loss of a multitubular reactor. When once coking is generated, the pressure loss further increases, creating a vicious cycle of a further acceleration of adhesion of the carbide to the catalyst surface, and the system may be eventually forced into a situation where the reaction is compelled to stop.

The present invention has been made to solve the problems above. More specifically, an object of the present invention is to provide a catalyst ensuring that in the case of causing gas-phase catalytic oxidation of an unsaturated aldehyde such as acrolein and an oxygen-containing gas by using the catalyst to produce a corresponding unsaturated carboxylic acid, coking can be suppressed by reducing the pressure loss and keeping the gas amount high and a corresponding unsaturated carboxylic acid can be produced at a high unsaturated aldehyde conversion rate with high selectivity.

Means for Solving the Problems

As a result of many intensive studies to solve the problem above, the present inventors have found that when a catalyst with the outer peripheral edge part being inclined relative to the center line is employed as the ring-shaped or columnar catalyst used at the time of causing gas-phase catalytic oxidation of an unsaturated aldehyde such as acrolein and an oxygen-containing gas to produce a corresponding unsaturated carboxylic acid, the pressure loss can be kept low, and an unsaturated carboxylic acid can be produced at a high unsaturated aldehyde conversion rate with high selectivity. The present invention has been accomplished based on this finding.

Namely, the present invention is described below.

[1] A ring-shaped or columnar catalyst, which is used at the time of producing a corresponding unsaturated carboxylic acid by causing gas-phase catalytic oxidation of an unsaturated aldehyde and an oxygen-containing gas, wherein the outer peripheral edge part is inclined relative to the center line.

[2] The catalyst according to [1], wherein the outer peripheral edge part is both end faces of the catalyst.

[3] The catalyst according to [1] or [2], wherein the angle at which the outer peripheral edge part is inclined relative to the center line is from 45 to 85°.

[4] The catalyst according to any one of [1] to [3], wherein
a ratio (a/b) of an outside diameter a (mm) to a bottom part diameter b (mm) is 2.3 or more,
a ratio (H/b) of a straight body part length H (mm) to the bottom part diameter b (mm) is 1.35 or more and 2.5 or less, the straight body part length H (mm) is from 2 to 11 mm, and the outside diameter a (mm) is from 2 to 11 mm.

[5] The catalyst according to [4], wherein a ratio (a/H) of the outside diameter a (mm) to the straight body part length H (mm) is 1.47 or more.

[6] A production method of acrylic acid, including causing a gas-phase catalytic oxidation of acrolein and an oxygen-containing gas by using the catalyst according to any one of [1] to [5].

[7] A production method of the catalyst according to any one of [1] to [5], including tablet molding.

Effect of the Invention

According to the catalyst of the present invention, in the case of producing an unsaturated carboxylic acid such as acrylic acid from an unsaturated aldehyde such as acrolein in a reactor filled with the catalyst, the pressure loss can be reduced and the gas amount can be kept high. Consequently, coking can be suppressed, and the unsaturated aldehyde such as acrolein can be oxidized at a high conversion rate, so that an unsaturated carboxylic acid such as acrylic acid can be produced with high selectivity.

In addition, the catalyst having been coked can be regenerated (decoking) by flowing an oxygen-containing gas. However, when a catalyst with the outer peripheral edge part being inclined relative to the center line is used as the ring-shaped or columnar catalyst, even if the catalyst is in the coked state, the effect of reducing the pressure loss can be maintained, in comparison with the catalyst in a conventional shape, and good decoking by a gas having the specific composition above can be realized.

MODE FOR CARRYING OUT THE INVENTION

Figure 1:
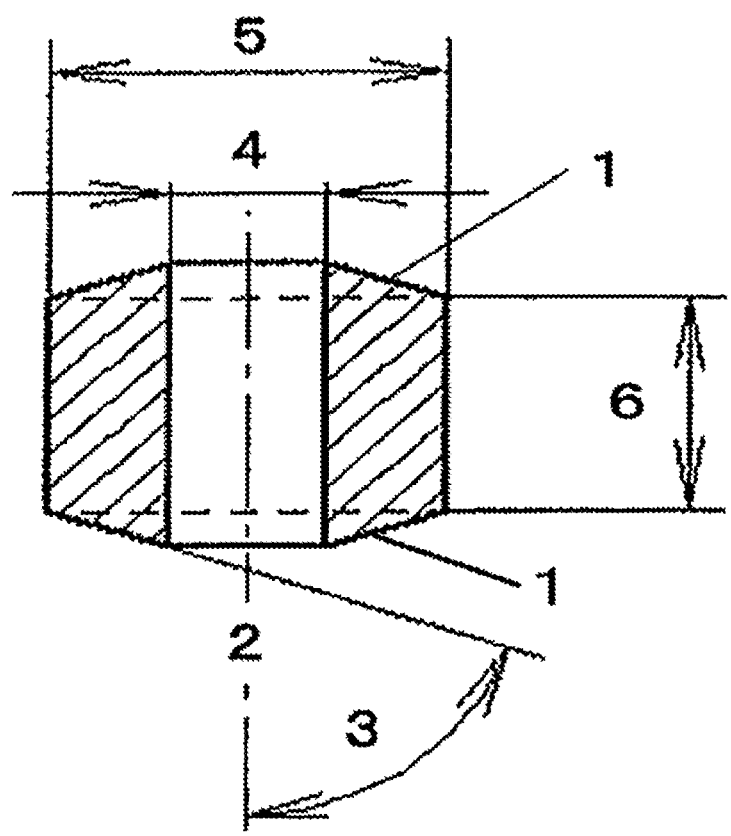
FIG. 1 is a transverse cross-sectional diagram of the ring-shaped catalyst of the present invention.

The present invention is described in detail below.

In this connection, each element of molybdenum (Mo), vanadium (V), niobium (Nb), tungsten (W), copper (Cu), magnesium (Mg), calcium (Ca), strontium (Sr), barium (Ba), zinc (Zn), antimony (Sb), iron (Fe), cobalt (Co), nickel (Ni), bismuth (Bi), and silicon (Si) is denoted by the element symbol in the parenthesis.

The catalyst of the present invention has a ring shape or a columnar shape, with the outer peripheral edge part being inclined relative to the center line. The outer peripheral edge part is inclined relative to the center line, so that when the catalyst is loaded in a reactor and an unsaturated carboxylic acid such as acrylic acid is produced from an unsaturated aldehyde such as acrolein, an unsaturated carboxylic acid such as acrylic acid can be produced, with high selectivity with reducing the pressure loss and increasing the conversion rate of an unsaturated aldehyde such as acrolein. In this connection, when a catalyst having a ring shape with the outer peripheral edge part being inclined relative to the center line and a catalyst having a columnar shape with the outer peripheral part being inclined relative to the center line are compared under the same volume of the catalysts, a catalyst having a ring shape with the outer peripheral edge part being inclined relative to the center line is preferred, because the area of the catalyst surface causing gas-phase catalytic oxidation of an unsaturated aldehyde and an oxygen-containing gas is large.

In the catalyst of the present invention, the outer peripheral edge part is inclined relative to the center line, and the outer peripheral edge part is preferably both end faces of the catalyst. When the outer peripheral edge part is both end faces of the catalyst, the fluidity of the catalyst particle is improved and at the time of loading the catalyst in a reactor by using a funnel, etc., bridging of the catalyst within the funnel is suppressed, and the catalyst is uniformly loaded into a reaction tube, so that the loading time can be shortened. Furthermore, in the case of, after the loading in a reactor, causing gas-phase catalytic oxidation of an unsaturated aldehyde such as acrolein and an oxygen-containing gas to produce corresponding unsaturated carboxylic acid, the pressure loss can be reduced. In addition, a corresponding unsaturated carboxylic acid can be produced with high selectivity by increasing the conversion rate of an unsaturated aldehyde.

The angle at which the outer peripheral edge part is inclined relative to the center line is preferably from 45 to 85°, more preferably from 55 to 80°, still more preferably from 65 to 75°. With an angle in this range, in the case of, after the loading in a reactor, causing gas-phase catalytic oxidation of an unsaturated aldehyde such as acrolein and an oxygen-containing gas to produce a corresponding unsaturated carboxylic acid, the pressure loss can be reduced. In addition, a corresponding unsaturated carboxylic acid can be produced with high selectivity by increasing the conversion rate of an unsaturated aldehyde.

In this connection, the angle at which the outer peripheral edge part is inclined relative to the center line can be described in the following. Irrespective of whether the catalyst has a ring shape or a columnar shape, the center line is parallel to the length direction of the straight body part. More specifically, the angle at which the outer peripheral edge part is inclined relative to the center line is an angle at which the outer peripheral edge part is inclined relative to the length direction of the straight body part.

In the catalyst of the present invention, it is preferred that the ratio (a/b) of the outside diameter a (mm) to the bottom part diameter b (mm) is 2.3 or more, the ratio (H/b) of the straight body part length H (mm) to the bottom part diameter b (mm) is 1.35 or more and 2.5 or less, the straight body part length H (mm) is from 2 to 11 mm, and the outside diameter a (mm) is from 2 to 11 mm.

Within the ranges above, cracks of the catalyst at the time of loading in a reactor can be prevented and in the case of causing gas-phase catalytic oxidation of an unsaturated aldehyde such as acrolein and an oxygen-containing gas to produce a corresponding unsaturated carboxylic acid, the pressure loss can be reduced. In addition, a corresponding unsaturated carboxylic acid can be produced with high selectivity by increasing the conversion rate of an unsaturated aldehyde.

The a/b is more preferably 2.35 or more, still more preferably 2.4 or more, and yet still more preferably 2.45 or more. Although the upper limit is not particularly limited, in view of catalyst strength, it is preferably 3.5.

The H/b is more preferably 1.4 or more and 2.5 or less, still more preferably 1.45 or more and 2.5 or less, and yet still more preferably 1.5 or more and 2.5 or less.

The H is more preferably from 2 to 10 mm, still more preferably from 2.3 to 9 mm, yet still more preferably from 2.6 to 7 mm, and most preferably from 3 to 5 mm.

The a is more preferably from 2 to 10 mm, still more preferably from 3 to 9 mm, yet still more preferably from 4 to 7 mm, and most preferably from 4 to 5.6 mm.

Furthermore, the ratio (a/H) of the outside diameter a (mm) to the straight body part length H (mm) is preferably 1.47 or more, more preferably 1.50 or more, still more preferably 1.53 or more, and yet still more preferably 1.56 or more. The upper limit is not particularly limited but is preferably 2.5. Within this range, in the case of causing gas-phase catalytic oxidation of an unsaturated aldehyde such as acrolein and an oxygen-containing gas to produce a corresponding unsaturated carboxylic acid, the pressure loss can be reduced. In addition, a corresponding unsaturated carboxylic acid can be produced with high selectivity by increasing the conversion rate of an unsaturated aldehyde.

The bottom part diameter, outside diameter and straight body part length are described by referring to the transverse cross-sectional diagrams (FIGS. 1 and 2) of the ring-shaped catalyst of the present invention. The catalyst of the present invention is a catalyst with the outer peripheral edge part being inclined relative to the center line, and the catalyst illustrated in FIG. 1 is a catalyst in which the inclination reaches the hollow body part of the ring, whereas the catalyst illustrated in FIG. 2 is a catalyst in which the inclination does not reach the hollow body part.

Figure 2:
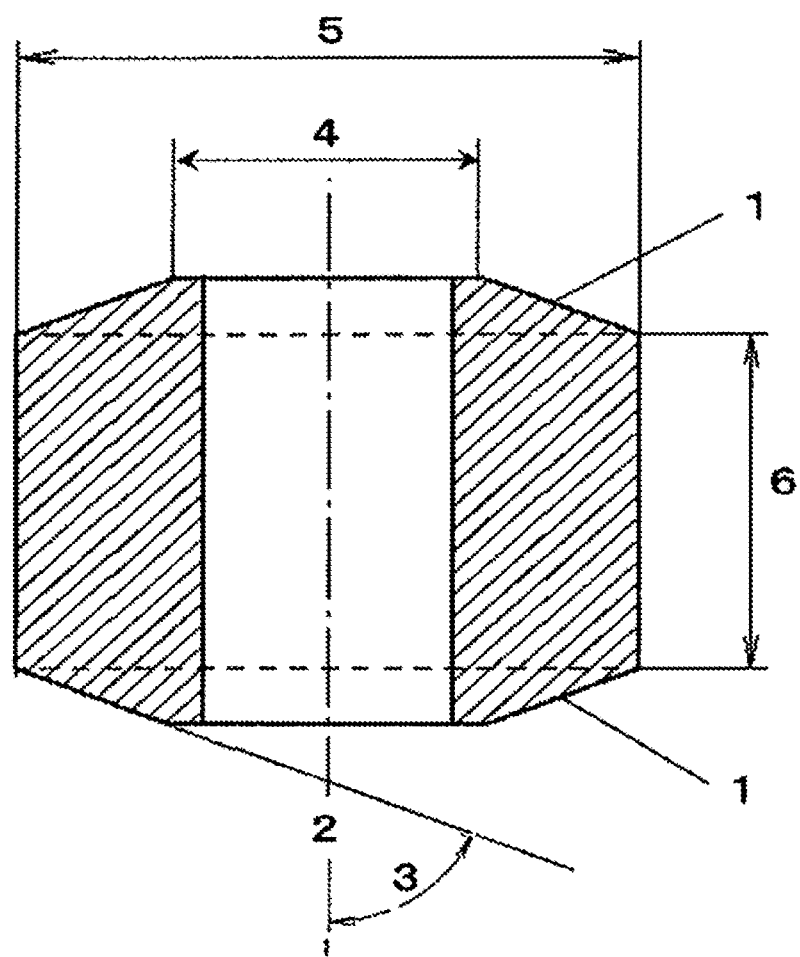
FIG. 2 is another transverse cross-sectional diagram of the ring-shaped catalyst of the present invention.

The straight body part length is the length excluding the inclined portion of the straight body part (see, FIGS. 1 and 2). The outside diameter is the diameter of the straight body part (see, FIGS. 1 and 2). The bottom part diameter is the diameter of the bottom part where the inclination is ended (see, FIGS. 1 and 2), irrespective of whether the inclination reaches the hollow body part of the ring (see, FIG. 1) or the inclination does not reach the hollow body part of the ring (see, FIG. 2).

As for the ring-shaped catalyst in the present invention, in comparison with the catalyst of FIG. 2, the catalyst of FIG. 1 has a large catalyst surface area for the catalyst volume and can produce a corresponding unsaturated carboxylic acid with high selectivity by increasing the conversion rate of an unsaturated aldehyde and therefore, a catalyst in which the inclination reaches the hollow body part is preferred.

In the case of a columnar catalyst, a hollow body part is not present and therefore, when FIGS. 1 and 2 are converted to a diagram of a columnar catalyst, the same diagram is obtained.

In this connection, in the catalyst of the present invention in examples of FIGS. 1 and 2, the outer peripheral edge part inclined relative to the center line is linear in the transverse cross-sectional diagram.

The catalyst of the present invention is a catalyst used for causing gas-phase catalytic oxidation of an unsaturated aldehyde such as acrolein and an oxygen-containing gas and thereby producing a corresponding unsaturated carboxylic acid and a catalyst containing at least molybdenum and vanadium is preferable. As long as the catalyst contains these two components, it is adaptable to the catalyst of the present invention. Among others, a catalyst represented by the following formula (1) can be preferably applied.

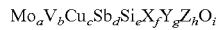  (1)

(In the formula, X is at least one element selected from the group consisting of Nb and W; Y is at least one element selected from the group consisting of Mg, Ca, Sr, Ba and Zn; Z is at least one element selected from the group consisting of Fe, Co, Ni and Bi; a to h represent a ratio of atomic numbers of respective elements and when a=12, 0<b≤12, 0<c≤12, 0≤d≤500, 0≤e≤500, 0≤f≤12, 0≤g≤8, and 0≤h≤500; and i is a numerical value satisfying the oxidation state of other elements).

The catalyst of the present invention is produced as follows, for example. A raw material compound containing respective element components of the catalyst above, in a predetermined amount required according to the composition produced, is appropriately dissolved or dispersed in an aqueous medium to produce a mixed solution containing catalyst components or an aqueous slurry thereof. As the raw material of each catalyst component, a nitrate, an ammonium salt, a hydroxide, an oxide, a sulfate, a carbonate, a halide, an acetate, etc. containing each element is used. For example, as the molybdenum, ammonium paramolybdate, molybdenum trioxide, molybdenum chloride, etc. is used, and as the vanadium, ammonium vanadate, vanadium pentoxide, vanadium oxalate, vanadium sulfate, etc. is used.

The mixed solution or aqueous slurry containing catalyst components is preferably stirred and mixed sufficiently so as to prevent uneven distribution of each component. Subsequently, the mixed solution or aqueous slurry containing catalyst components is dried to form a powder, and the drying can be conducted by various methods. Examples thereof include drying by a normal spray drier, slurry drier, drum drier, etc., and, among others, drying by a spray drier is preferred.

The powder obtained by drying is then molded in a ring shape or a columnar shape. The method for molding in a ring shape or a columnar shape is not particularly limited and preferably includes tablet molding, extrusion molding, etc. Above all, tablet molding is preferred, since the degree of inclination of the outer peripheral edge part is easily controlled. At the time of molding, a molding aid may be used. The molding aid is preferably silica, graphite, crystalline cellulose, cellulose, starch, polyvinyl alcohol, stearic acid or stearate. The molding aid can be usually used in an amount of approximately from 0.1 to 50 parts by weight per 100 parts by weight of the powder. In addition, an inorganic fiber such as ceramic fiber and whisker can also be used, if desired, as a material for enhancing the mechanical strength of the catalyst. The use amount of such a fiber is usually from 1 to 30 parts by weight per 100 parts by weight of the powder.

EXAMPLES

Although the present invention is described more specifically below by referring to Examples, the present invention is not limited to the following Examples as long as its gist is observed.

Example 1

Preparation of Catalyst

A catalyst in which constituent components except for oxygen are blended to give the composition shown in Table 1 was produced. The amount of each supply source compound used is the amount shown in Table 1.

Basic nickel carbonate was dispersed in 350 ml of pure water, and silica and antimony trioxide were added and fully stirred to obtain a slurry-like liquid.

The slurry-like liquid was concentrated by heating and dried. The obtained dry solid was fired at 800° C. for 3 hours in a muffle furnace, and the produced solid was pulverized to obtain a powder capable of passing through a 60-mesh sieve (Sb—Ni—Si—O powder).

On the other hand, pure water was heated to 80° C., and ammonium paramolybdate and ammonium metavanadate were sequentially dissolved with stirring. An aqueous copper sulfate solution prepared by dissolving copper sulfate in 100 ml of pure water was added thereto, and niobium hydroxide was further added and stirred to obtain a slurry liquid.

Figure 3:
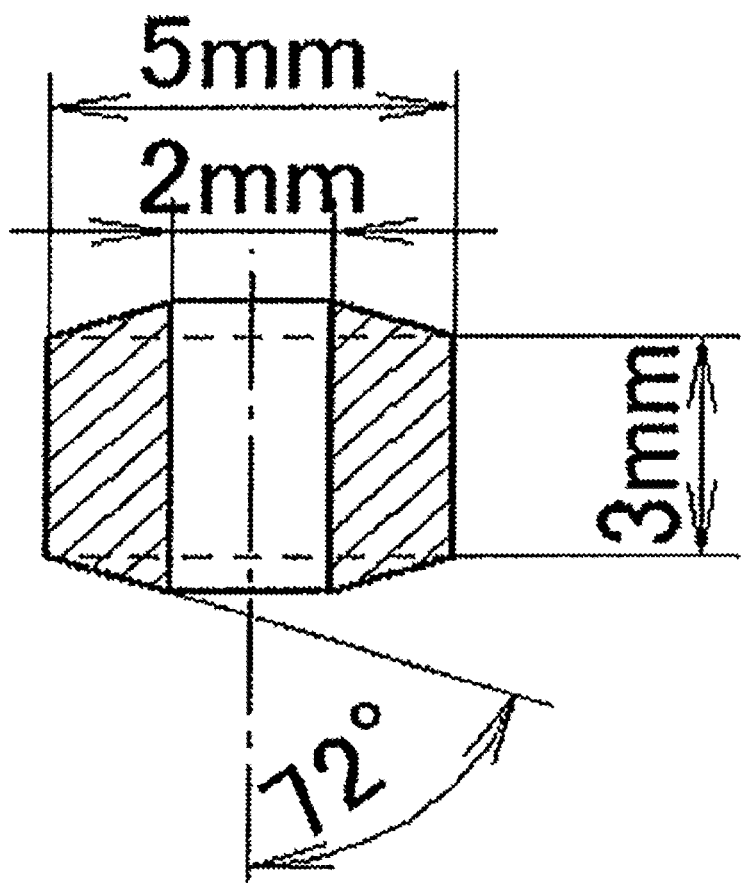
FIG. 3 is a transverse cross-sectional diagram illustrating one example of the ring-shaped catalyst of the present invention.
Figure 4:
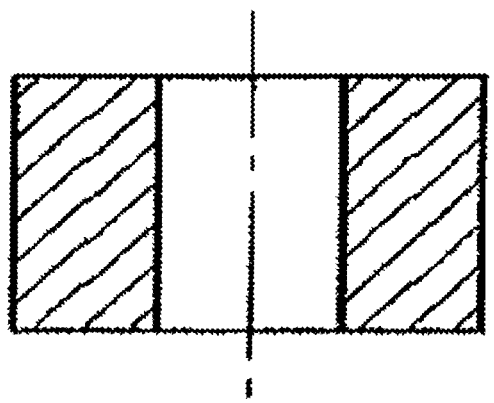
FIG. 4 is a transverse cross-sectional diagram of the conventional catalyst.

The Sb—Ni—Si—O powder was gradually added to the slurry liquid with stirring and fully stirred and mixed to obtain a slurry-like liquid. The obtained slurry-like liquid was spray-dried at 150° C. to obtain a precursor compound. Thereto, 1.5 wt % of graphite was added and mixed, and the mixture was molded in a ring shape with a density of 2.93 g/cm$^3$ by a small size tableting mold machine. The resulting molded body was fired at 380° C. in a 1% oxygen flow to produce a catalyst. In the ring-shaped catalyst, as illustrated in the transverse cross-sectional diagram of FIG. 3, outside diameter: 5 mm; bottom part diameter: 2 mm; straight body part length: 3 mm; the outer peripheral edge part was inclined relative to the center line on both end faces; and the inclination angle relative to the center line was 72° in both. In addition, the pressure loss of the catalyst was measured by the following method. The results are shown in Table 2.

Measurement of Pressure Loss

An acrylic resin-made straight tube having an inside diameter of 26 mm and a length of 1,000 mm was stood upright, and the ring-shaped catalyst above was loaded to a height of 900 mm. Through a SUS-made piping having an inside diameter of 6 mm attached to the top of the acrylic resin-made straight tube, dry air was flowed at a flow rate of 50 NL/min, and the differential pressure was measured by digital differential pressure gauge testo 506-3 attached to a piping branched from the SUS-made piping (differential pressure A). Subsequently, the ring-shaped catalyst particles were withdrawn from the acrylic resin-made straight tube to form an empty tube, and the differential pressure was measured in the same manner and taken as the blank value. The pressure loss was determined as (differential pressure A)—blank value.

Gas-Phase Catalytic Oxidation Reaction of Acrolein

Thereafter, a gas-phase catalytic oxidation reaction of acrolein was performed using the catalyst above with continuing the following conditions. The acrolein conversion rate, acrylic acid selectivity, and acrylic acid yield are defined as in the following formula (1) to (3).

Acrolein conversion rate (mol %)=100×(molar number of acrolein reacted)/(molar number of acrolein supplied)   (1)

Acrylic acid selectivity (mol %)=100×(molar number of acrylic acid produced)/(molar number of acrolein converted)   (2)

Acrylic acid yield (mol %)=100×(molar number of acrylic acid produced)/(molar number of acrolein supplied)   (3)

In a reaction tube (inside diameter: 21 mm) with a jacket containing niter, 33 ml of the catalyst above was loaded, and gas-phase catalytic oxidation reaction of acrolein was conducted by heating the reaction tube; introducing a composition gas (acrolein: 6 vol %, oxygen: 8 vol %, steam: 22 vol %, nitrogen gas: 64 vol %); and setting SV (space velocity: flow rate of raw material gas per unit time/apparent volume of catalyst loaded) at 1,550/hr. The results are shown together in Table 3.

The niter is a heating medium composed of a nitrate of alkali metal, and this heating medium melts at 200° C. or more; can be used up to 400° C.; has good heat removal efficiency and therefore, is suitable for an oxidation reaction generating a large amount of heat.

Example 2

A catalyst was obtained in the same manner as in Example 1 except that in the ring-shaped catalyst, outside diameter: 5 mm, bottom part diameter: 2 mm, and straight body part length: 2 mm. In addition, the pressure loss was measured by the same method as in Example 1. The results are shown in Table 2. Subsequently, a gas-phase catalytic oxidation reaction of acrolein was conducted in the same manner as in Example 1. The results are shown together in Table 3.

Example 3

A catalyst was obtained in the same manner as in Example 1 except that in the ring-shaped catalyst, outside diameter: 5 mm, bottom part diameter: 2 mm, and straight body part length: 5.1 mm. In addition, the pressure loss was measured by the same method as in Example 1. The results are shown in Table 2. Subsequently, a gas-phase catalytic oxidation reaction of acrolein was conducted in the same manner as in Example 1. The results are shown together in Table 3.

Comparative Example 1

A catalyst was obtained in the same manner as in Example 1 except that in the ring-shaped catalyst, outside diameter: 5 mm, bottom part diameter: 2 mm, straight body part length: 3 mm, and the outer peripheral edge part was not inclined relative to the center line in both end parts. In addition, the pressure loss was measured by the same method as in Example 1. The results are shown in Table 2. Subsequently, a gas-phase catalytic oxidation reaction of acrolein was conducted in the same manner as in Example 1. The results are shown together in Table 3.

TABLE 1

| | Catalyst Composition (atom ratio) | | | | | | |
| --- | --- | --- | --- | --- | --- | --- | --- |
| | Mo | V | Nb | Cu | Ni | Sb | Si |
| Examples 1 to 3 Comparative Example | 12 | 2.4 | 1 | 1.2 | 8.5 | 20 | 2 |

TABLE 2

| | Example 1 | Example 2 | Example 3 | Comparative Example 1 |
| --- | --- | --- | --- | --- |
| Pressure loss (hPa) | 43 | 44 | 31 | 51 |

TABLE 3

|  | Reaction Temperature (° C.) | Acrolein Conversion Rate (mol %) | Acrylic Acid Selectivity (mol %) | Acrylic Acid Yield (mol %) |
|---|---|---|---|---|
| Example 1 | 245 | 99.8 | 93.0 | 92.8 |
| Example 2 | 240 | 99.9 | 92.2 | 92.1 |
| Example 3 | 245 | 99.5 | 92.7 | 92.3 |
| Comparative Example 1 | 245 | 99.6 | 92.2 | 91.8 |

According to the catalyst of the present invention, as described above, in the case of causing gas-phase catalytic oxidation of acrolein as an unsaturated aldehyde in a reactor filled with the catalyst and thereby producing acrylic acid as a corresponding unsaturated carboxylic acid, the pressure loss can be kept low and at the same time, acrolein can be oxidized at a high conversion rate without raising the temperature, so that acrylic acid can be produced with high selectivity.

In this connection, the pressure loss in Examples 1 to 3 shows superiority to the conventional technique by the measurement of simply flowing dry air, and it is apparent that the superiority of the present invention is maintained also in the case of flowing a raw material mixed gas including an unsaturated aldehyde such as acrolein and an oxygen-containing gas.

While the invention has been described in detail and with reference to specific embodiments thereof, it will be apparent to one skilled in the art that various changes and modifications can be made therein without departing from the spirit and scope of the invention. This application is based on Japanese Patent Application (Patent Application No. 2017-098451) filed on May 17, 2017, Japanese Patent Application (Patent Application No. 2017-098452) filed on May 17, 2017, Japanese Patent Application (Patent Application No. 2017-088647) filed on Apr. 27, 2017, and Japanese Patent Application (Patent Application No. 2016-145419) filed on Jul. 25, 2016, the contents of which are incorporated herein by way of reference.

DESCRIPTION OF REFERENCE NUMERALS AND SIGNS

1 Outer peripheral edge part
2 Center line
3 Angle at which inclined
4 Bottom part diameter
5 Outside diameter
6 Straight body part length

The invention claimed is:

1. A ring-shaped or columnar catalyst, which is used at the time of producing a corresponding unsaturated carboxylic acid by causing gas-phase catalytic oxidation of an unsaturated aldehyde and an oxygen-containing gas, wherein an outer peripheral edge part is inclined relative to a center line,
   a ratio (a/b) of an outside diameter a (mm) to a bottom part diameter b (mm) is 2.3 or more,
   a ratio (a/H) of the outside diameter a (mm) to a straight body part length H (mm) is 1.47 or more, and,
   the straight body part length H (mm) is from 3 to 11 mm.

2. The catalyst according to claim 1, wherein the outer peripheral edge part is both end faces of the catalyst.

3. The catalyst according to claim 1, wherein an angle at which the outer peripheral edge part is inclined relative to the center line is from 45 to 85°.

4. The catalyst according to claim 1, wherein a ratio (H/b) of the straight body part length H (mm) to the bottom part diameter b (mm) is 1.35 or more and 2.5 or less.

5. The catalyst according to claim 1, wherein the outside diameter a (mm) is from 2 to 11 mm.

* * * * *